United States Patent [19]

Okamoto et al.

[11] Patent Number: 4,593,121

[45] Date of Patent: Jun. 3, 1986

[54] NOVEL ACRYLATES AND THEIR MANUFACTURING METHODS

[75] Inventors: Yasuhiro Okamoto; Takashi Watanabe; Motonobu Kubo, all of Iwakuni, Japan

[73] Assignee: Sanyo-Kokusaku Pulp Co., Ltd., Tokyo, Japan

[21] Appl. No.: 776,867

[22] Filed: Sep. 17, 1985

[30] Foreign Application Priority Data

Feb. 26, 1985 [JP] Japan ................... 60-36956

[51] Int. Cl.$^4$ ............................................. C07C 69/00
[52] U.S. Cl. ..................................................... 560/144
[58] Field of Search ......................................... 560/144

*Primary Examiner*—Paul R. Michl
*Assistant Examiner*—Alex H. Walker
*Attorney, Agent, or Firm*—Oblon, Fisher, Spivak, McClelland & Maier

[57] ABSTRACT

Acrylates represented by a following general formula (I).

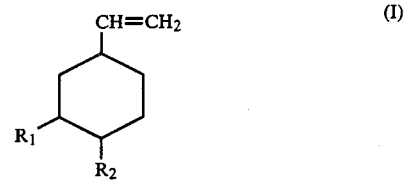

[wherein $R_1$ and $R_2$ indicate —OH or

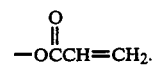

However, a case of $R_1 = R_2 =$ —OH is excluded.] and manufacturing methods for the same.

3 Claims, No Drawings

NOVEL ACRYLATES AND THEIR MANUFACTURING METHODS

DETAILED DESCRIPTION OF THE INVENTION

A. Utilizable fields in the industry

The present invention relates to novel acrylates represented by a formula (I)

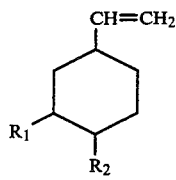
(I)

[wherein $R_1$ and $R_2$ indicate —OH or

However, a case of $R_1 = R_2 = $—OH is excluded.] and their manufacturing methods.

The compounds represented by the formula (I) can be subjected to the homopolymerization or the copolymerization with other compounds containing unsaturated groups in the presence of heat, ultraviolet radiation, and radical polymerization initiator.

B. Conventional techniques

Up to this time, various types of acrylates are known. For example, monofunctional monomers such as methyl methacrylate, ethyl acrylate, 2-ethylhexyl acrylate, etc. and multifunctional monomers such as trimethylolpropane triacrylate, trimethylolpropane trimethacrylate, pentaerythritol triacrylate, etc. are known in general.

C. Problems to be solved by the invention

However, when using for printing inks and paints, the monofunctional monomers are problematic because of a heavy offensive smell of unreacted monomer after the curing. While, the multifunctional monomers have a shortcoming that they are necessary to be used in large quantities to the resin when using as the diluents for paints and printing inks, and therefore, the desirable characteristics of the resin are lost.

D. Means to solve the problem, action and effect

As a result of diligent studies, the inventors have obtained novel acrylates represented by the aforementioned formula (I) which have low viscosity and low offensive smell and a solubility to the various resins. These are useful as the raw materials or the modifiers of inks, paints, adhesives, covering agents and molding compounds.

The compounds of the invention (I) can be manufactured by the method described below. Namely, they are obtained through the esterification of 1,2-dihydroxy-4-vinylcyclo-hexane represented by a formula (II)

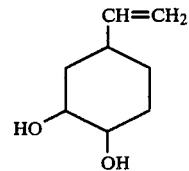

with acrylic acid or acrylic acid derivatives. Through this esterification, a mixture of 1(or 2)-acryloyloxy-2(or 1)-hydroxy-4-vinylcyclohexane (hereinafter abbreviated as compound (III) represented by a formula (III)

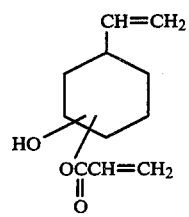

with 1,2-diacryloyloxy-4-vinylcyclohexane (hereinafter abbreviated as compound (IV)) represented by a formula (IV)

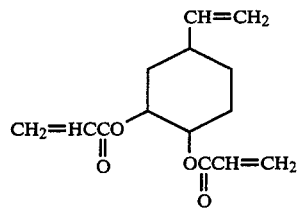

can be obtained.

Also, compound (IV) can be obtained through the esterification of compound (III) with acrylic acid or acrylic acid derivatives.

When the esterification was performed by using acrylic acid, either of sulfuric acid and p-toluenesulfonic acid can be used as the catalyst. Moreover, as polymerization inhibitors used in the reaction process, those capable of being removed easily by washing with aqueous solution of alkali of the substances such as hydroquinone, hydroquinone monomethyl ether, cuprous chloride, etc. are preferable.

As the azeotropic solvents to be used for removing water formed during the esterification reaction from the system, organic solvents which form azeotropic mixtures with water and which are immiscible mutually with water substantially such as benzene, toluene, xylene, n-hexane, methyl isobutyl ketone, etc. can be used independently or as mixtures.

It is also possible to manufacture compound (I) through the transesterification between acrylates and compound (II). In this case, the transesterification is carried out by heating wellknown acryates such as methyl, ethyl, buthyl, n-propyl, or iso-propyl acrylates with compounds (II) in the presense of polymerization inhibitors and catalysts, followed by removing the corresponding lower alcohols produced, from the system.

As the polymerization inhibitors in this case, hydroquinone, hydroquinone monomethyl ether, etc. are used when using sulfuric acid or p-toluenesulfonic acid as the transesterification catalyst, but alkaline polymerization inhibitors, for example, p-phenylenediamine and phenyl-β-naphthylamine are used when using alkaline catalysts such as metallic sodium, sodium alcoholate, etc.

E. Examples

In following, the invention will be illustrated using examples.

EXAMPLE 1

In a reaction vessel equipped with a reflux condenser, a water separator and a stirrer, 142 g of compound (II), 173 g of acrylic acid, 9 g of p-toluenesulfonic acid, 6 g of hydroquinone monomethyl ether and 400 ml of toluene were placed, and the mixture was heated for 3 hours under stirring. After separated water from toluene-water distillates in the water separator, toluene was returned continuously to the reaction vessel. During this period, 27 g of water was obtained. After the reaction, the product was cooled to room temperature, washed twice with 500 ml of saturated aqueous solution of sodium carbonate, and then washing was repeated with saturated brine until the alkalinity had disappeared. To this solution 7 g of 1,1′-bi-2-naphthol was added, and the vacuum distillation was carried out to obtain 69 g of compound (III) as a fraction with a boiling point of 125°–130° C./1 mmHg and 75 g of compound (IV) as a fraction with a boiling point of 130°–135° C./1 mmHg. Infrared spectra and nuclear magnetic resonance spectra for these compounds are shown in Table 1 and Table 2, respectively.

EXAMPLE 2

Except that 392 g of compound (III) were used in place of compound (II) in Example 1 and the heating time was made 18 hours, similar procedure was taken to that described in Example 1 to obtain 285 g of compound (IV), that is, 1,2-diacryloyloxy-4-vinylcyclohexane.

EXAMPLE 3

In a reaction vessel equipped with vigreax type fractionating column and a capillary through which nitrogen gas could be babbled from the bottom of the vessel were placed 142 g of compound (II), 860 g of methyl acrylate, 25 g of hydroquinone monomethyl ether and 9 g of p-toluenesulfonic acid. The mixture was heated to boiling in oil bath and the reflux was continued. Methanol formed was allowed to distill off forming azeotropic mixture with methyl acrylate.

After the reaction for 10 hours, excess methyl acrylate was allowed to distill off and the product was cooled to room temperature. This was washed twice with 500 ml of saturated aqueous solution of sodium carbonate, then washed with saturated brine until the alkalinity had disappeared, and dried over anhydrous sodium sulfate. To this solution were added 14 g of 1,1′-bi-2-naphthol, and the vacuum distillation was carried out to obtain 59 g of compound (III) as a fraction with a boiling point of 125°–130° C./1 mmHg and 70 g of compound (IV) as a fraction with a boiling point of 130°–135° C./1 mmHg.

TABLE 1

Infrared absorption spectra (liquid film)

| Fraction | Wave number [cm$^{-1}$] | Type of absorption | |
|---|---|---|---|
| (III) | 3460 | Hydroxyl group O—H | stretching vibration |
| | 1720 | Acryloyl group C=O | stretching vibraition |
| | 1630 | End vinyl group C=C | stretching vibration |
| | 1400 | Acryloyl group C=C | in-plane symmetric deformation vibration |
| | 1180 | Ester linkage C—O | stretching vibration |
| (IV) | 1720 | Acryloyl group C=O | stretching vibration |
| | 1630 | End vinyl group C=C | stretching vibration |
| | 1400 | Acryloyl group C=C | in-plane symmetric deformation vibration |
| | 1180 | Ester linkage C—O | stretching vibration |

TABLE 2

Nuclear magnetic resonance spectra ($^{13}$C-NMR, 89.55 Mz, CDCl$_3$)

| Fraction | | Mark | δ (ppm) |
|---|---|---|---|
| (III) | | a | 130.6 |
| | | b | 128.6 |
| | | c | 165.6 |
| | | d | 113.4, 113.1 |
| | | e | 142.4, 141.9 |
| | | f | 73.9, 73.1 |
| | | g | 68.0, 67.0 |
| | | h | 35.5, 34.6 |
| | | i | 34.8–24.8 |
| (IV) | | a | 130.0 |
| | | b | 127.7 |
| | | c | 164.3 |
| | | d | 113.4 |
| | | e | 141.2 |
| | | f | 70.0, 69.2 |
| | | g | 34.3 |
| | | h | 31.6, 26.0, 25.1 |

What is claimed is:

1. Acrylates represented by a following general formula (I),

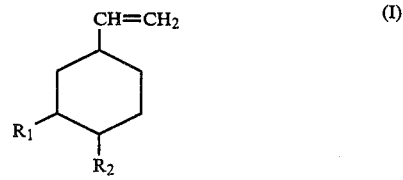

(I)

wherein R$_1$ and R$_2$ indicate —OH or

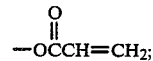

however, a case of R$_1$=R$_2$=—OH is excluded.

2. A manufacturing method for acrylates represented by the following general formula (I),

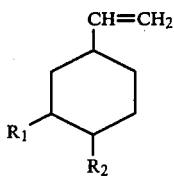 (I)

wherein $R_1$ and $R_2$ indicate —OH or

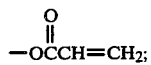

however, a case of $R_1=R_2=$—OH is excluded; characterized in that 1,2-dihydroxy-4-vinylcyclohexane is allowed to react with acrylic acid or acrylic acid derivatives.

3. A manufacturing method for 1,2-diacryloyloxy-4-vinylcylcohexane represented by the following general formula (I)

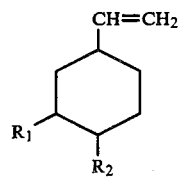 (I)

wherein both $R_1$ and $R_2$ indicate

characterized in that 1(or 2)-acryloyloxy-2(or 1)-hydroxy-4-vinylcyclohexane is allowed to react with acrylic acid or acrylic acid derivatives.

* * * * *